United States Patent [19]

Farooq et al.

[11] 4,064,263
[45] Dec. 20, 1977

[54] 4,5-BENZOSPIRO(2,4)-HEPTANE (AND HEPTA-4,6-DIENE)-1-CARBOXYLIC ACID ESTERS AND COMPOSITIONS CONTAINING SAME

[75] Inventors: Saleem Farooq, Aesch; Jozef Drabek, Allschwil; Laurenz Gsell, Fullinsdorf; Friedrich Karrer, Zofingen; Willy Meyer, Riehen, all of Switzerland

[73] Assignee: Ciba-Geigy Corporation, Ardsley, N.Y.

[21] Appl. No.: 723,682

[22] Filed: Sept. 16, 1976

[30] Foreign Application Priority Data

Sept. 26, 1975 Switzerland .................. 12565/75
July 23, 1976 Switzerland .................. 9465/76

[51] Int. Cl.$^2$ .............................. A01N 9/28
[52] U.S. Cl. .................. 424/285; 260/347.4
[58] Field of Search .............. 260/347.4; 424/285

[56] References Cited

U.S. PATENT DOCUMENTS 3,823,117  7/1974  Fanta et al. .................. 260/468 G
3,962,458  6/1976  Schrider .................. 424/304

*Primary Examiner*—Henry R. Jiles
*Assistant Examiner*—Bernard Dentz
*Attorney, Agent, or Firm*—Harry Falber

[57] ABSTRACT

2,2-Dimethyl-4,5-benzospiro(2,4)-heptane-1-carboxylic acid esters and 2,2-dimethyl-4,5-benzospiro(2,4)hepta-4,6-diene-1-carboxylic acid esters of the formula

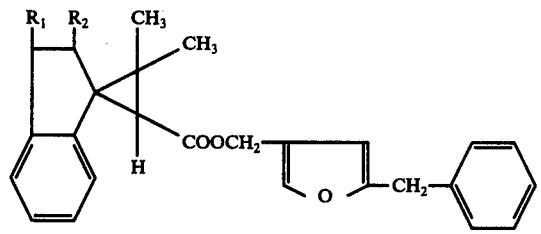

wherein $R_1$ and $R_2$ are each hydrogen or together are a carbon-carbon bond, processes for producing them and their use in combatting pests.

5 Claims, No Drawings

4,5-BENZOSPIRO(2,4)-HEPTANE (AND HEPTA-4,6-DIENE)-1-CARBOXYLIC ACID ESTERS AND COMPOSITIONS CONTAINING SAME

The present invention relates to 2,2-dimethyl-4,5-benzospiro(2,4)heptane-1-carboxylic acid esters and 2,2-dimethyl-4,5-benzospiro(2,4)hepta-4,6-diene-1-carboxylic acid esters, to processes for producing them and to their use in combatting pests.

The esters according to the invention have the formula

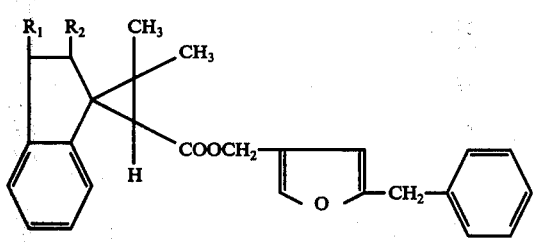

wherein $R_1$ and $R_2$ are each hydrogen or together are a carbon-carbon bond.

The compounds of formula I are obtained by methods known per se: for example they are obtained a. by reacting a compound of formula II

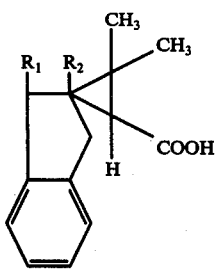

with a compound of formula III

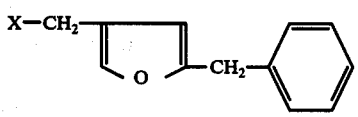

in the presence of a base;

b. by reacting a compound of formula IV

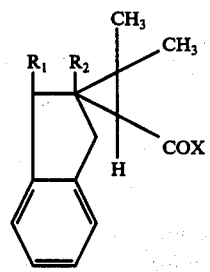

with the compound of formula V

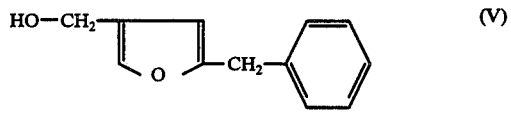

in the presence of a base; or c. by treating a compound of the above formula II with a compound of the above formula V in the presence of dicyclohexylcarbodiimide; whereby in the formulae II to V, the symbols $R_1$ and $R_2$ have the meanings given under formula I, and X is a halogen atom, especially a chlorine or bromine atom.

The processes (a) to (c) are performed at a reaction temperature between $-10°$ and $150°$ C, usually between $20°$ and $80°$ C, at normal or elevated pressure, and preferably in a solvent or diluent inert to the reactants.

Suitable solvents or diluents for these reactions are, e.g., ethers and ethereal compounds such as diethyl ether, diisopropyl ether, dioxane, dimethoxyethane and tetrahydrofuran; ketones such as acetone and methyl ethyl ketone; aliphatic, aromatic as well as halogenated hydrocarbons, especially benzene, toluene, xylenes, chloroform, chlorobenzene and methylene chloride; as well as dimethylformamide, dimethylsulphoxide and hexamethylphosphoric acid triamide.

Bases suitable for the processes (a) and (b) are, in particular, tertiary amines such as triethylamine, dimethylaniline, pyridine, picolines and lutidines; also hydroxides, oxides, carbonates and bicarbonates of alkali metals and alkaline-earth metals, as well as alkali metal alcoholates, such as potassium-t.-butylate and sodium methylate.

The derivatives of formulae II to V used as starting materials are known; see, e.g., U.S. Pat. No. 3,823,177.

The compounds of formula I are present in different optically active isomers as well as cis/trans isomers, unless in production individual isomers have been used as starting materials. The various stable isomeric mixtures can be separated, for example, by recrystallisation or by chromatographical separation methods into the individual isomeric forms, for example by gas-chromatography or by adsorption on a separating material having selective adsorption activity, such as silica gel or aluminum oxide, and subsequent elution of the separated isomers with a suitable solvent.

It is understood that the present invention embraces both separate cis/trans isomers or optically active isomers and mixtures thereof.

The compounds of formula I have a broad biocidal action and can be used for combatting various plant and animal pests; for example they can be used as acaricides, insecticides, ectoparasiticides, nematocides, fungicides, plant-growth regulators or herbicides.

In particular, however, the active substances of formula I are suitable for combatting insects of the families: Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestididae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae; and they are especially suitable for combatting insects that damage plants in crops of fruit, vegetables and cotton (such as *Spodoptera littoralis, Heliothis virescens* and *Myzus per-*

*sicae*), as well as for combatting house flies (such as *Musca domestica*).

Furthermore, the compounds of formula I have an unusually very favourable action against members of the order Acarina, e.g. against ticks and mites of the families: Ixodidae, Argasidae, Tetranychidae and Dermanysidae.

The acaricidal or insecticidal action can be substantially broadened and adapted to suit given conditions by the addition of other insecticides and/or acaricides. Suitable additives are, for example: organic phosphorus compounds; nitrophenols and derivatives thereof; formamidines; ureas; pyrethrin-like compounds; as well as carbamates and chlorinated hydrocarbons.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in the art.

The compositions according to the invention are produced in a manner known per se by the intimate mixing and/or grinding of active substances of formula I with suitable carriers, optionally with the addition of dispersing agents or solvents which are inert to the active substances. The active substances can be obtained and used in the following forms:
solid preparations:
    dusts, scattering agents, granulates (coated granulates, impregnated granulates and homogeneous granulates);
liquid preparations:

(a)

water-dispersible concentrates of active substance: wettable powders, pastes or emulsions;

(b)

solutions.

The content of active substance in the above-described compositions is between 0.1 and 95%.

The active substances of formula I can be formulated for example as follows:
Dusts:
The following substances are used in the preparation of (a) a 5% dust and (b) a 2% dust:

(a)

5 parts of Active Substance,
95 parts of talcum;

(b)

2 parts of Active Substance,
1 part of highly dispersed silicic acid,
97 parts of talcum.

The active substances are mixed and ground with the carriers.
Granulate:
The following substances are used to produce a 5% granulate:
5 parts of Active Substance,
0.25 part of epichlorohydrin,
0.25 part of cetyl polyglycol ether,
3.50 parts of polyethylene glycol,
91 parts of kaolin (particle size 0.3 - 0.8 mm).

The active substance is mixed with epichlorohydrin and dissolved with 6 parts of acetone; the polyethylene glycol and cetyl polyglycol ether are then added. The solution obtained in this manner is subsequently sprayed onto kaolin, and the acetone is evaporated off in vacuo.
Wettable powders:
The following constituents are used to produce (a) a 40%, (b) and (c) a 25%, and (d) a 10% wettable powder:

(a)

40 parts of Active Substance,
5 parts of sodium lignin sulphonate,
1 part of sodium dibutyl-naphthalene sulphonate,
54 parts of silicic acid;

(b)

25 parts of Active Substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(c)

25 parts of Active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)

10 parts of Active Substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in the appropriate mills and rollers. Wettable powders are obtained which can be diluted with water to give suspensions of the required concentration.
Emulsifiable concentrates:
The following substances are used to produce (a) a 10% (b) a 25%, and (c) a 50% emulsifiable concentrate:

(a)

10 parts of Active Substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)

25 parts of Active Substance,
2.5 parts of epoxidised vegetable oil,
10 parts of alkylarylsulphonate/fatty alcohol polyglycol ether mixture, 5 parts of dimethylformamide,
57.5 parts of xylene;

(c)

50 parts of Active Substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of the required concentration.

Sprays:

The following constituents are used to produce (a) a 5% spray, and (b) a 95% spray:

(a)

5 parts of Active Substance,
1 part of epichlorohydrin,
94 parts of ligroin (boiling limits 160°–190° C);

(b)

95 parts of Active Substance,
5 parts of epichlorohydrin.

The invention is further illustrated by the following Examples.

EXAMPLE 1

Production of 2-benzyl-furan-4-yl-methyl-2', 2'-dimethyl-4',5'-benzospiro(2',4')hepta-4',6'-diene-1'-carboxylate To a solution of 4.4 g (0.0205 mole) of 2,2-dimethyl-4,5-benzospiro(2,4)hepta-4,6-diene-1-carboxylic acid in 50 ml of hexamethylphosphoric acid triamide is added 3.1 g (0.022 mole) of potassium carbonate. An addition is then made dropwise of 4.15 g (0.02 mole) of 2-benzyl-4-chloromethyl-furan, and the reaction mixture is stirred for 18 hours at room temperature. In further processing, the reaction mixture is poured into water and extracted with ether. The ether phase is subsequently washed twice with water and twice with saturated sodium chloride solution. After drying over sodium sulphate, the solvent is distilled off and the oily residue is purified by column-chromatography (silica gel/ether/hexane = 1 : 4) to obtain the product of the formula

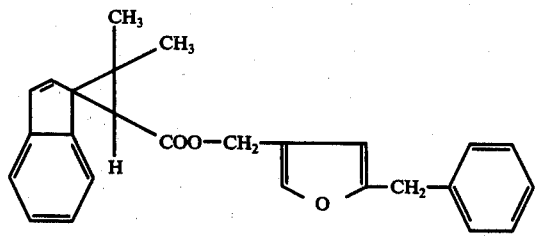

as a diastereomeric mixture: $n_D^{20} = 1.5842$.

The compounds of the following formula are produced in an analogous manner:

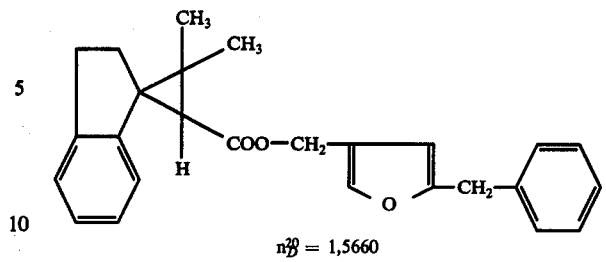

$n_D^{20} = 1.5660$

EXAMPLE 2

Stomach poison action against Spodoptera littoralis, Heliothis virescens and Leptinotarsa decemlineata Cotton plants and potato plants were sprayed with a 0.05% aqueous emulsion of active substance (obtained from a 10% emulsfiable concentrate).

After the coating had been dried, the cotton plants were infested with Spodoptera littoralis and Heliothis virescens larvae $L_3$, respectively; and the potato plants with Colorada beetle larvae (Leptinotarsa decemlineata). The test was carried out at 24° C with 60% relative humidity.

The compounds according to Example 1 exhibited in the above test a good insecticidal stomach poison action against Spodoptera littoralis, Heliothis virescens and Leptinotarsa decemlineata larvae.

EXAMPLE 3

Action against Chilo suppressalis

Rice plants of the Caloro species were planted 6 plants per pot in plastic pots having an upper diameter of 17 cm, and were grown to a height of about 60 cm. Infestation with Chilo suppressalis larvae ($L_1$; 3–4 mm long) was effected 2 days after addition of the active substance in granular form (applied amount equivalent to 8 kg of active substance per hectare) to the paddy water. An evaluation of the insecticidal action was made 10 days after addition of the granulate.

The compounds according to Example 1 were effective in the above test against Chilo suppressalis.

EXAMPLE 4

Acaricidal action

Phaseolus vulgaris (plants) were infested, 12 hours before the test for acaricidal action, with an infested piece of leaf from a mass culture of Tetranychus urticae. The transferred mobile stages were sprayed with the emulsified test preparations from a chromatography-sprayer in a manner ensuring no overflow of the spray liquor. An assessment was made after 2 and 7 days, by examination under a binocular microscope, of living larvae and dead larvae, adults and eggs, and the results were expressed in percentages. The treated plants were kept during the "holding time" in greenhouse compartments at 25° C. The compounds according to Example 1 were effective in the above test against adults, larvae and eggs of Tetranychus urticae.

We claim:

1. A compound of formula I

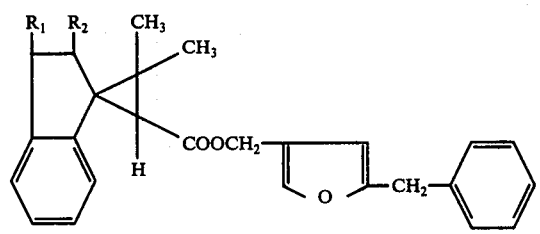

(I)

wherein $R_1$ and $R_2$ are each a hydrogen atom, or together are a carbon-carbon bond.

2. The compound according to claim 1 of the formula

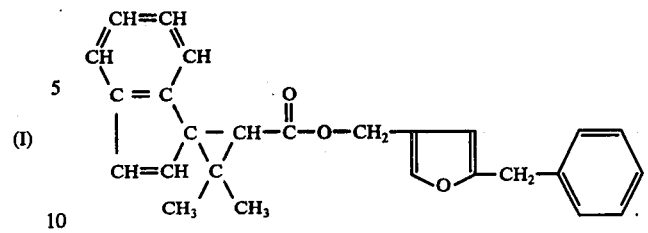

3. The compound according to claim 1 of the formula

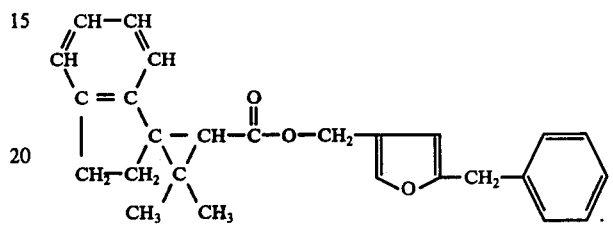

4. An insecticidal and acaricidal composition comprising an insecticidally and acaricidally effective amount of a compound of the formula of claim 1, together with a suitable carrier therefor.

5. A method for combatting insects and acarids which comprises applying to the locus thereof an insecticidally and acaricidally effective amount of a compound of the formula of claim 1.